(12) United States Patent
Bindszus et al.

(10) Patent No.: US 9,655,554 B2
(45) Date of Patent: May 23, 2017

(54) DEVICE AND METHOD FOR MONITORING MOVEMENT AND ORIENTATION OF THE DEVICE

(71) Applicant: KONINKLIJKE PHILIPS N.V., Eindhoven (NL)

(72) Inventors: Andreas Bindszus, Boeblingen (DE); Willem Verkruijsse, Veldhoven (NL); Ihor Olehovych Kirenko, Eindhoven (NL); Marek Janusz Bartula, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 472 days.

(21) Appl. No.: 14/352,080

(22) PCT Filed: Oct. 15, 2012

(86) PCT No.: PCT/IB2012/055593
§ 371 (c)(1),
(2) Date: Apr. 16, 2014

(87) PCT Pub. No.: WO2013/057648
PCT Pub. Date: Apr. 25, 2013

(65) Prior Publication Data
US 2014/0243682 A1    Aug. 28, 2014

Related U.S. Application Data

(60) Provisional application No. 61/549,366, filed on Oct. 20, 2011.

(51) Int. Cl.
*G06K 9/00* (2006.01)
*A61B 5/18* (2006.01)
(Continued)

(52) U.S. Cl.
CPC .............. *A61B 5/18* (2013.01); *A61B 5/0075* (2013.01); *A61B 5/0077* (2013.01); *A61B 5/08* (2013.01);
(Continued)

(58) Field of Classification Search
CPC ....... A61B 5/0059; A61B 5/05; A61B 5/0075; A61B 5/00; A61B 5/0803; G06T 7/00
(Continued)

(56) References Cited

U.S. PATENT DOCUMENTS

| 7,142,191 B2 * | 11/2006 | Idesawa | G06F 1/1601 |
| | | | 345/156 |
| 7,365,793 B2 * | 4/2008 | Cheatle | H04N 7/18 |
| | | | 348/373 |

(Continued)

FOREIGN PATENT DOCUMENTS

| DE | 3040452 A1 | 5/1982 |
| DE | 102005059687 A1 | 6/2007 |

(Continued)

*Primary Examiner* — Abolfazl Tabatabai (57) ABSTRACT

The present invention relates to a device and method for monitoring movement and orientation of the device, comprising an imaging unit (10) for obtaining images over time, a holding means (12, 13) for holding said imaging unit to obtain images from the surroundings of the device, and a processing unit (14) for detecting movement and orientation of the device by detecting changes in subsequently obtained images.

15 Claims, 5 Drawing Sheets

(51) Int. Cl.
  *A61B 5/00* (2006.01)
  *A61B 5/08* (2006.01)
  *A61B 5/113* (2006.01)
  *G06T 7/246* (2017.01)
  *H04N 5/225* (2006.01)

(52) U.S. Cl.
  CPC .......... *A61B 5/0816* (2013.01); *A61B 5/1135* (2013.01); *A61B 5/6802* (2013.01); *A61B 5/6823* (2013.01); *A61B 5/6831* (2013.01); *A61B 5/6835* (2013.01); *A61B 5/6893* (2013.01); *G06T 7/246* (2017.01); *A61B 5/6805* (2013.01); *A61B 2503/22* (2013.01); *A61B 2503/40* (2013.01); *A61B 2505/03* (2013.01); *A61B 2562/0219* (2013.01); *A61B 2576/00* (2013.01); *G06T 2207/10016* (2013.01); *G06T 2207/30076* (2013.01); *G06T 2207/30241* (2013.01)

(58) Field of Classification Search
  USPC .......... 382/103, 107, 236, 128–134; 348/169–172, 352
  See application file for complete search history.

(56) References Cited

U.S. PATENT DOCUMENTS

| | | | |
|---|---|---|---|
| 8,174,580 B2* | 5/2012 | Hayashi | H04N 5/232 348/169 |
| 2006/0058613 A1 | 3/2006 | Nakai | |
| 2008/0071177 A1 | 3/2008 | Yanagidaira | |
| 2008/0137960 A1 | 6/2008 | Lee et al. | |
| 2010/0061596 A1 | 3/2010 | Mostafavi et al. | |
| 2010/0098403 A1* | 4/2010 | Sones | G03B 13/02 396/383 |
| 2011/0144517 A1 | 6/2011 | Cervantes | |

FOREIGN PATENT DOCUMENTS

| | | |
|---|---|---|
| EP | 1645840 A1 | 4/2006 |
| EP | 1749477 A1 | 2/2007 |
| JP | 2005322077 A | 11/2005 |
| JP | 2011024960 A | 2/2011 |
| WO | 2007085241 A1 | 8/2007 |
| WO | 2009040711 A2 | 4/2009 |
| WO | 2010066824 A2 | 6/2010 |
| WO | 2010100677 A1 | 9/2010 |

* cited by examiner

DEVICE AND METHOD FOR MONITORING MOVEMENT AND ORIENTATION OF THE DEVICE

CROSS-REFERENCE TO PRIOR APPLICATIONS

This application is the U.S. National Phase application under 35 U.S.C. §371 of International Application No. PCT/IB2012/055593, filed on Oct. 15, 2012, which claims the benefit of U.S. Provisional Patent Application No. 61/549,366, filed on Oct. 20, 2011. These applications are hereby incorporated by reference herein.

FIELD OF THE INVENTION

The present invention relates to a device and method for monitoring movement and orientation of the device. Further, the present invention relates to a processor and processing method for use in such a device. Finally, the present invention relates to a computer program for implementing said processing method on a computer.

BACKGROUND OF THE INVENTION

Respiration rate (RR) and respiration volume (RV) are vital signs to be monitored in hospitalized or bedridden patients. Measurement of RR and/or RV is currently not performed at all, rather inaccurately, or in a time consuming way (e.g. by a nurse who counts inhalations of a patient over a defined period of time, then records the metric in a chart, manually). Automated methods are therefore desirable.

Known systems and methods particularly use tension belts mounted around the chest, accelerometers placed on the chest or cameras aimed at the chest equipped with video analysis algorithms. Besides the general monitoring of RR for bedridden patients, it is likely of great interest to perform detailed sleep studies.

Other modern devices, such as smart phones or cameras, also comprise a three-axis accelerometer or gyroscope for determining movements and orientation of the device, for instance to switch the display shown in the screen to the correct orientation.

SUMMARY OF THE INVENTION

It is an object of the present invention to provide a device and method for monitoring movement and orientation of the device in a simple manner without the need for separate hardware elements.

It is a further object of the present invention to enable monitoring of a subject's respiration without intruding the privacy of a patient, but provides a high sensitivity and may, preferably, also allow measurement of the respiration volume in addition to measurement of the respiration rate. Further, a corresponding processor, processing method and computer program shall be provided.

In a first aspect of the present invention a device is presented comprising:
an imaging unit for obtaining images over time,
a holding means for holding said imaging unit to obtain images from the surroundings of the device, and
a processing unit for detecting movement and orientation of the device by detecting changes in subsequently obtained images.

In a further aspect of the present invention a processor is presented for use in a device for monitoring movement and orientation of the device, comprising an imaging unit for obtaining images over time and a holding means for holding said imaging unit to obtain images from the surroundings of the device, said processor being configured to detect movement and orientation of the device by detecting changes in subsequently obtained images.

In yet another aspect of the present invention, there is provided a computer program which comprises program code means for causing a computer to perform the steps of the processing method when said computer program is carried out on a computer.

Preferred embodiments of the invention are defined in the dependent claims. It shall be understood that the claimed methods, processor, and computer program have similar and/or identical preferred embodiments as the claimed device and as defined in the dependent claims.

It has been found by the present invention provides that a functionality similar to the functionality of a three-axis accelerometer or a gyroscope, as present in modern smart phones, can be provided by means of an imaging unit, such as a simple camera. A known three-axis accelerometer embedded into a device (e.g. smart phone) generally measures motion and orientation of the device in space. Generally, the same information (movement and orientation) can, however, also be obtained by evaluating subsequently obtained images to detect from changes between subsequent images if the device has moved and in which direction it has or how the orientation of the device is compared to a previous orientation.

The invention is not only able to detection motion of the device itself, but by attaching the device to an object in a way that the device experiences the same movements as the object, it is possible to detect the motion of the object by evaluating images data as explained above. Hereby, it is to be noted that the device needs to be attached to the object in such a way, that the imaging unit is facing away from the object and takes images of the surroundings of the object. In other words, there is no direct (visual) detection of movement of the object by simply observing the object by the imaging unit, but changes in the images taken of the surroundings are evaluated.

In particular, according to the present invention, by observing changes in subsequently obtained images from the surroundings of the device (and/or object), e.g. the ceiling, the wall, any devices in the room, shadows or other characteristic (fixed) marks on the ceiling or wall, etc., information about the movement of the device/object can be indirectly monitored.

In this context, it shall be noted that the detection of movement may include the detection of acceleration of the device. Further, the term "object" does not only cover non-living devices, but also includes living subject (humans, animals, plants), i.e. the invention may also be used to detection movements and/or orientations of subjects. Still further, it shall be noted that the processing unit must not necessarily be embedded into the same common entity or housing like the imaging unit and holding means, but may also be arranged separately there from and may be connected (wired or wireless) to the imaging unit for receiving the image data.

Generally, by embedding the present invention into stand-alone dedicated devices or smart phones, it can be used for many different applications, including healthcare and lifestyle applications. For example, sleep phase alarm clocks use accelerometric sensors to detect movement of a sleeper, so that it can wake the person when he/she is not in REM (Rapid Eye Movement) phase, therefore awakes more easily.

According to a preferred embodiment said processing unit is configured to detect periodic displacements of one or more features of the surroundings, in particular static marks or gradients of light, in the obtained images for detecting movement, in particular acceleration and/or periodic movement, of the device.

The imaging unit may be configured to continuously or at regular intervals obtain images, in particular to obtain still images or video data by use of a still image camera, video camera and/or infrared camera. An infrared camera is preferably useful to obtain image data during night time or in dark rooms. The user may be given the option at which intervals images shall be obtained. This may depend from the situation where the proposed system and method shall be used. For instance, if used in an ICU (intensive care unit) environment for patient monitoring, the respiration monitoring will be done continuously, while for observation of the health status or to provide an information if the person is alive, particularly of elderly people, monitoring only a few times of day and night might be sufficient.

In general, the frequency of images could be dependent on the expected frequency of the measured signal. For example, the frequency of respiration is not expected to be >60 breathes per minute; a sufficient frame-rate for respiration monitoring can be 15 frames per second. In order to measure a rate of the extracted signal, at least two periods of the signal should be observed. For example, for respiration that means a preferred minimal temporal period of about 2 seconds or 30 frames. Ideally, the maximum temporal window size should be flexible, to adjust any low rate of respiration (e.g. 2-3 breathes per minute).

As mentioned above, said holding means preferably comprises a holder for placing the imaging unit or the device onto an object such that the imaging unit is facing away from the object.

According to a preferred embodiment said holding means comprises a holder for placing the imaging unit or the device onto a subject's chest, in particular onto a clothing or a cover covering the subject's chest, such that the imaging unit is facing away from the subject's chest to obtain images from the surroundings of the subject, and said processing unit is configured to detect periodic movements of the subject's chest caused by respiration by detecting changes in subsequently obtained images and to determining the subject's respiration rate and/or respiration volume from the detected movements of the subject's chest. For instance, in a practical embodiment multiple cameras are embedded in a small blanket-like object which allows estimation of not only RR but also RV. Placement of the blanket on a patient's chest will cause each camera to be roughly perpendicular to the patient's chest. Together, the cameras' images provide 3D information regarding the patient's curvature and thus volume changes over time (comparable to multiple cameras placed at different positions on a balloon that is inflated). The imaging unit or the device can be position also on a bed, in a vicinity of the monitored person. In this case, the device would measure motion of a bed, induced by the respiratory motion of the patient.

It has been found that in the known camera based systems for measuring the RR the camera is generally directed to the chest of the patient to monitor the chest movements. However, in particular for prolonged (continuous) monitoring, a camera aimed at the patient may cause the patient to feel that his/her privacy is intruded upon. This problem is avoided by the present invention and the intrusion of privacy is strongly diminished or even prevented completely by aiming the imaging unit, e.g. a camera, away from the subject (e.g. a patient).

According to this embodiment of the present invention the RR (and possible RV) is thus not derived from image data of the subject itself, but from changes in subsequently obtained images from the surroundings of the subject. Thus, information about the movement of the subject's chest can be indirectly monitored. From said (indirectly) obtained information about the chest movements the desired information on the subject's respiration can be derived.

Since known accelerometers that are used according to a known method for respiration measurement measure acceleration (not displacement) slow deep inhalations may be missed or misinterpreted as poor respiration. The proposed monitoring system is more sensitive for such motions, particularly since the proposed arrangement of the imaging unit, i.e. close to or on chest looking away from the subject, enhances any small angular motions into relatively large displacements of the imaged area so that changes of the image over time are clearly visible.

Thus, according to this embodiment of the present invention, the imaging unit, e.g. one or more image sensors, positioned on the chest and aimed away from the subject, record images of the surroundings. Respiration induced periodic movements of the chest thus translate into periodic changes in the recorded images. The combination of these images, e.g. video streams, is used to derive the RR from the periodic changes and/or the RV from the geometrical information of the image unit's positions, which can preferably also be determined from the recorded images.

As mentioned, said processing unit is preferably configured to determine the subject's respiration rate from the period of detected changes in subsequently obtained images and/or to determine the subject's respiration volume from the strength of changes, in particular the intensity of displacements of one or more features of the surroundings, in subsequently obtained images.

To further increase the strength of (angular) movement of the imaging unit a side of the holder facing the subject is curved, in particular in the form of a hemisphere. Movements of the chest are thus "amplified" due to the curvature of the holder.

In a preferred embodiment said monitoring system further comprises an acceleration measurement unit for determining the acceleration of movements of the subject, wherein said processing unit is configured to distinguish period movement of the subject caused by respiration from other movements of the body from the obtained images and to determine the respiration of the subject from the determined acceleration of said periodic movements of the subject caused by respiration. This allows distinguishing between movements of the subject (in particular the chest) caused by respiration and other movements that may also lead to changes in the obtained images, which latter changes shall not be evaluated for determining the RR and/or RV.

In an advanced embodiment said imaging unit comprises at least two imaging elements, e.g. image sensors or cameras, arranged on said holder for individually obtaining images of the subject's surroundings and said processing unit is configured to determine the respiration volume of the subject by analyzing differences of the changes in said individually obtained images. Particularly the strength of the changes observed in images obtained from different imaging elements allows determining the amount of motion of the chest which is then used to derive information on the respiration volume.

Preferably, said holder is integrated into a cover covering the subject's chest, in particular into a blanket. This easily allows a continuous monitoring, e.g. in an ICU environment, without having any impact on the patient's freedom of movement. Preferably, many imaging elements are used, e.g. integrated into the blanket, so that there is at least one imaging element positioned above the patient's chest.

In still another embodiment said holder is integrated into a seatbelt of a vehicle, and said processing unit is configured to detect motion of the hands of a subject that is secured by said seatbelt from the obtained images and to detect drowsiness of the subject from the detected motion of the subject's hands and the determined respiration rate and/or respiration volume of the subject. This allows use of the invention in a different field of application, particularly as a safety feature in cars, trucks, trains, airplanes, etc. where it must be made sure that the user (i.e. the driver, pilot, . . . ) is alive, awake and watchful. This can be ensured by use of the present invention.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1A:
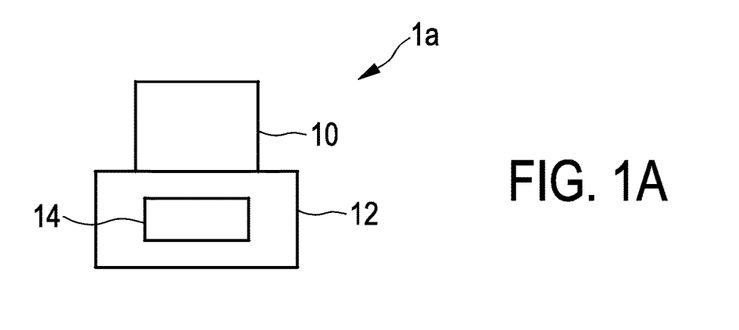
FIG. 1 shows schematic layouts of three embodiments of the device according to the present invention.
Figure 1B:
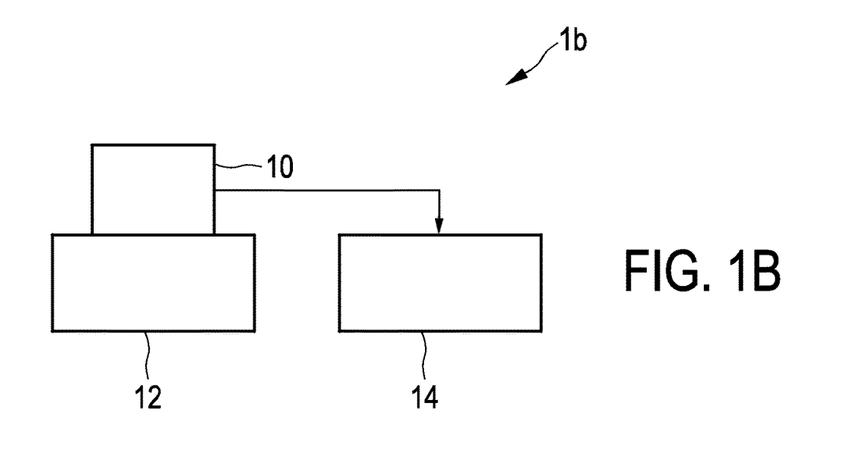
Figure 1C:
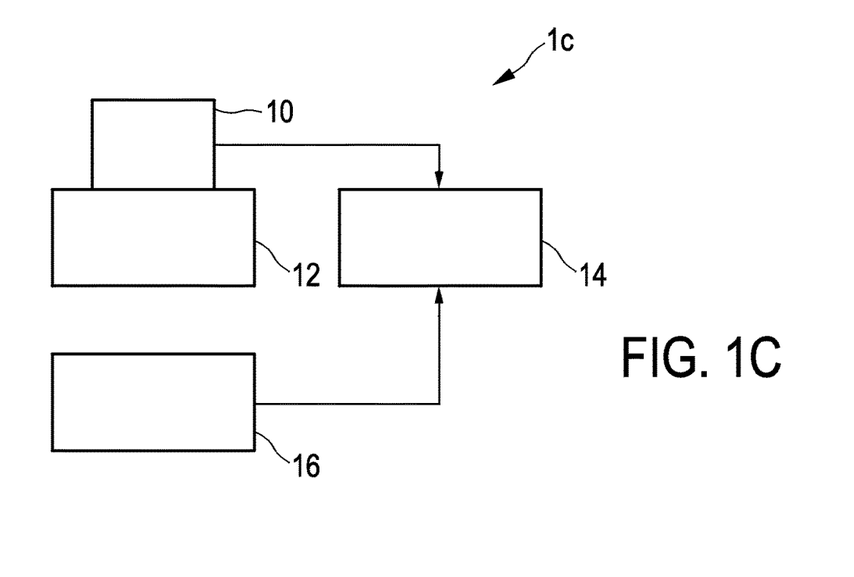

FIG. 1 shows schematic layouts of three embodiments of the device 1a, 1b, 1c according to the present invention. Such a device may be a respiration monitoring system directed to the monitoring of a patient's respiration (mainly respiration rate and/or respiration volume, but also respiration or non-respiration). Such a respiration monitoring system can be applied for monitoring the respiration of any subject, i.e. persons (e.g. elderly persons living at home or in a special-care home) or animals (e.g. in a medical station for animals). Many further applications of such a device are possible as will be explained below.

Generally, the device 1a, 1b, 1c for monitoring movement and orientation of the device comprises an imaging unit 10 for obtaining images over time, a holding means 12 for holding said imaging unit to obtain images from the surroundings of the device (at least static image features), and a processing unit 14 for detecting movement and orientation of the device by detecting changes (at least of static image features) in subsequently obtained images. The observed changes in the images, in particular the displacements of the static image features can be translated into changes of the position and/or orientation of the device.

In the first embodiment of the device 1a the processing unit 14 is included in the holding means 12 (e.g. a mechanical holder for holding the camera representing the imaging unit 10). Alternatively, the processing unit 14 may be included in the imaging unit 10. In the second embodiment of the device 1b the processing unit 14 is arranged outside of the holding means 12, e.g. as a separate device in the same or a different room to which the image data are transmitted from the imaging unit 10 by any kind of connection (wired, wireless, mixed, . . . ).

In the third embodiment of the device 1c, which is quite similar to the second embodiment of the device 1b an additional movement sensor 16, in particular an acceleration sensor, is provided by which respiration movements of an object to which said device 1c (or at least the imaging unit 10) is attached, can be distinguished from other movements of the object (e.g. small rotation) so that only images obtained during movements to be detected (e.g. periodic respiratory movements in case of monitoring the respiration of a patient) can be selected and used to determine the information.

Figure 2:
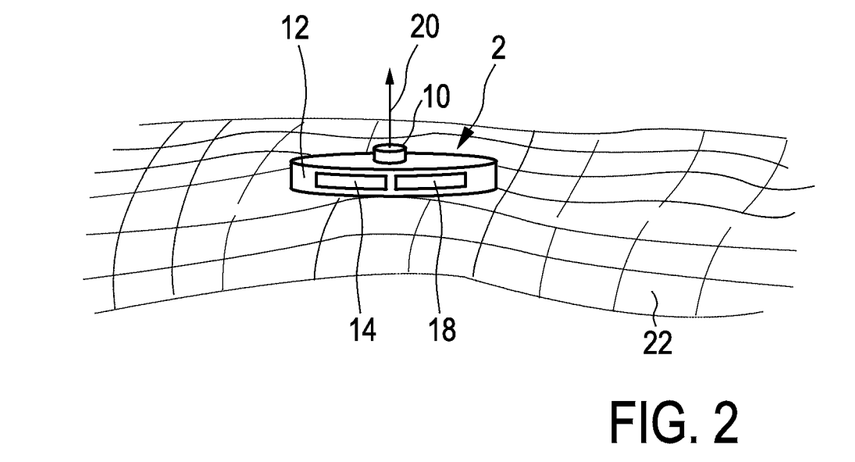
FIG. 2 illustrates a first way of arrangement of the proposed device for a first application as respiration monitoring device.

FIG. 2 illustrates a first implementation of the first embodiment of the device 1a for a respiration monitoring, where all elements of the device 1a are implemented as a single device 2. As an example, the imaging unit 10 may be a simple imaging sensor, e.g. a low-cost video camera. The imaging sensor 10 is built on the holder 12, which contains the processing unit 14 and further (for a real implementation required, but for the present invention not essential) elements 18 like drivers, batteries and memory. The device 2 should be placed on a chest of a subject to ensure upward imaging sensor orientation (i.e. facing away from the subject; indicated by arrow 20) such that the imaging sensor 10 views the ceiling or wall features. It should be noted that "upward" and "facing away from the subject" should be interpreted broadly, i.e. it is not required that the viewing direction is exactly 90° to the surface of the subject, but a slightly sideways orientation is acceptable and would not diminish the functionality of the device. Further, the device 2 can but does not require a direct contact with the subject's body and can be placed on a blanket 22 or clothes, as shown in FIG. 2.

According to the present invention the imaging unit 10 automatically detects within the obtained images any marks or other characteristics (static image features) in the surroundings (e.g. on ceiling or walls) and analyses displacements of those marks over time in subsequently obtained images. In the absence of features, any static (not moving) gradient in light intensity on a ceiling or walls can be used as well as a mark. Rooms without such gradients are virtually non-existent in practice.

For breathing monitoring a preferred frame rate may be between 5 and 20 frames per second. However, in general, the frame rate depends on the kind of application and may be higher or lower than this number. Mainly the expected rate according to which the observed characteristics change determines the frame rate. Sufficient periods of the changes should be observed to have a higher reliability of the obtained result.

Figure 3A:
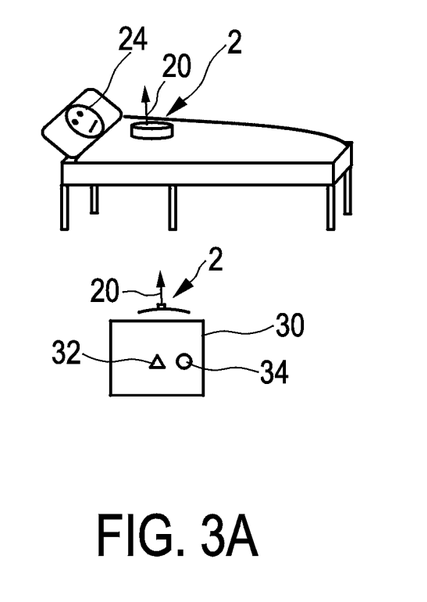
FIG. 3 illustrates the general function of a first embodiment of the proposed respiration monitoring device.

The displacement measured by the imaging unit 10 will correspond to the motion of the chest during inhalation or exhalation, as shown in FIG. 3. FIG. 3A shows the exhaled state, where the torso of the patient 24 is in normal state and the imaging unit 10 points ("looks") upwards. FIG. 3A also shows a side view of the device 2 and an example of a (ceiling) image 30 including, as schematic examples for detected marks, a triangle 32 and a circle 34.

Figure 3B:
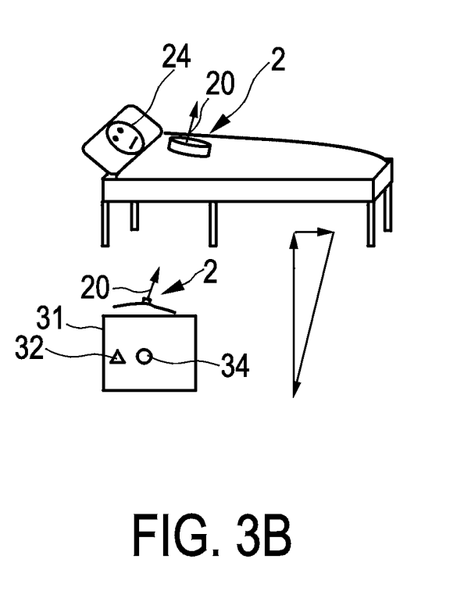

FIG. 3B shows the inhaled state, where the torso of the patient 24 is in an expanded (or curved) state and the imaging unit 10 points ("looks") more sidewards. As indicated by the changed image 31 the displacement of the image 31, indicated by the changed positions of the marks 32, 34, is very sensitive for small angular changes, as also indicated by the shown vector diagram. Any, even very small displacements of the detected marks 32, 34 will thus be detected by the device 2. The size of the displacement corresponds to the amount of motion during inhaling and exhaling.

Figure 4:
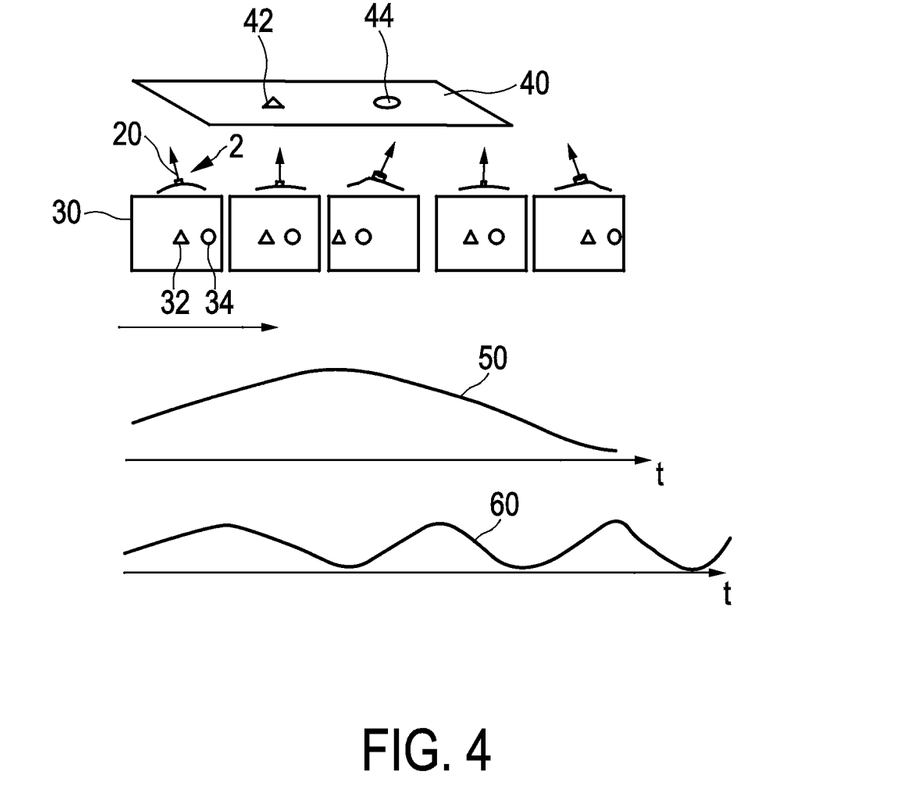
FIG. 4 illustrates the extraction of a respiration signal by use of the first embodiment of the proposed respiration monitoring device.

Respiration causes repetitive motion of chest and/or belly. The proposed device, being placed on a chest of a person, can register repetitive motion of marks and generate a signal, which corresponds to the respiration signal, as shown in FIG. 4. The first row shows an exemplary scenario on the ceiling of a room including, as exemplary marks, a triangle 42 and a circle 44. In the second row side views of the device 2 over time for different states over a single respiration cycle are shown. In the third row the obtained images 30 including the imaged marks 32, 34 are shown. In the fourth row a displacement signal 50 indicating the relative displacement of the imaged marks 32, 34 is indicated over time. In the fifth row a derived respiration cycle signal 60 is shown indicating the counted respiration cycles on a longer time scale, which respiration cycle signal 60 finally represents or allows retrieving the respiration rate.

The sensitivity of the measurement can be increased by amplifying the motion of a camera by means of curved (e.g. hemisphere) surface of the back of the device.

Figure 5A:
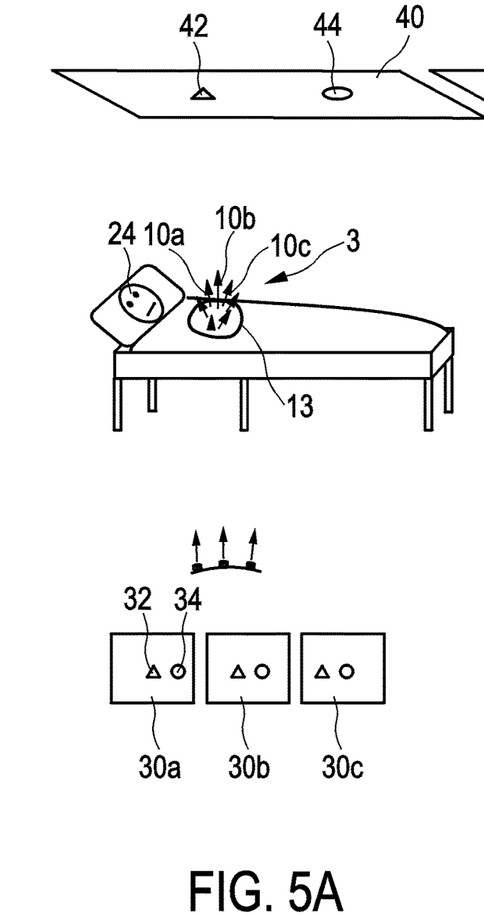
FIG. 5 illustrates the general function of a second embodiment of the proposed respiration monitoring device.

In another embodiment of the proposed device, implemented as a respiration monitoring device 3, at least two imaging units 10a, 10b, 10c (see FIG. 5) are used, placed e.g. at one flexible platform 13. This embodiment allows measurement of a respiratory volume (RV) by analyzing the difference in spatial displacement detected by the different imaging units 10a, 10b, 10c as indicated in FIG. 5. FIG. 5A shows the exhaled state, where the torso of the patient 24 is in normal state and most imaging units 10a, 10b, 10c point ("look") substantially upwards. FIG. 5A also shows a side view of the device 3 and an example of three (ceiling) images 30a, 30b, 30c taken by the imaging units 10a, 10b, 10c.

Figure 5B:
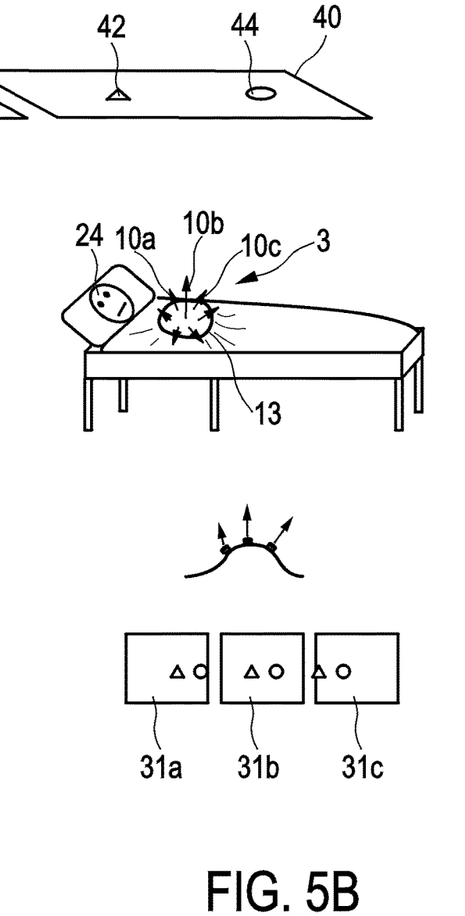

FIG. 5B shows the inhaled state, where the torso of the patient 24 is in an expanded (or curved) state. The imaging units 10a, 10b, 10c point ("look") more sidewards and at least some imaging units 10a, 10b, 10c are aimed laterally. As indicated by the changed images 31a, 31b, 31c the displacements of the images 31a, 31b, 31c, indicated by the changed positions of the marks 32, 34, depend on the actual position of the respective imaging units 10a, 10b, 10c.

According to a further embodiment a flexible platform carrying or including several imaging units is embedded into a blanket, particularly in a part of it located near a chest of a person. In this case, a long-term monitoring of a sleep quality is possible by means of combined analysis of respiratory motion, actigraphy (motion of body parts) and/or illumination conditions during the sleep, which can all be collected by the imaging units.

An important advantage of the proposed invention is that it can be installed into any camera device so that it can add the functionality of a three-axis accelerometer to that device (e.g. low cost camera phone, web cam, photo camera, barcode scanner etc. or a dedicated device). There are more devices, which have a camera, than devices with an embedded accelerometer. Using the proposed invention all those camera devices can, for instance, be enriched with a computer program (software) functionality of an accelerometer implemented as proposed herein.

The proposed invention can be used in several applications for spot-check or continuous monitoring of respiration (e.g. for sleep monitoring). The main use case scenario might be a spot-check of respiration of a patient by placing the proposed device on the top of a blanket, near the chest of a patient. In this case, respiratory measurement can be provided without a hassle of fixing a chest belt on around a patient's body, as is currently done and which is time consuming and disturbing to a patient.

It shall also be noted that the proposed video-based monitoring can be combined with other methods for respiration monitoring (e.g. accelerometer-based) for improvement of motion robustness. Still further, the proposed method of respiration monitoring can be embedded into another camera-based monitor or in a bar-code scanner. Many patient monitors come with bar-code scanners already today in order to scan patient ID wrist bands or barcode labels on medications for security purposes to make sure patient data and medication are assigned or administered to the right patient. Those bar-code scanners are indeed video cameras which can be used for taking regular images besides their original intention to scan bar-codes. Therefore a bar-code scanner that comes with a patient monitor to read wrist band IDs from patients can also be used to detect patient respiration. Then the measurement of respiration can be done either in a conventional way, i.e. by pointing a camera towards a subject, or in a way proposed according to the present invention in case a subject objects a conventional way of monitoring due to privacy issues.

In some embodiments the live image data can be accessed remotely, thus providing a visual check from a remote location through a (wired or wireless, e.g. WLAN) connection to the camera to verify whether the "sensor" is still in the right place and pointing to the right target area. In other words, it is very easy to remotely control the correctness of measurements without adding extra dedicated hardware. This functionality cannot be provided with a conventional accelerometer.

Figure 6:
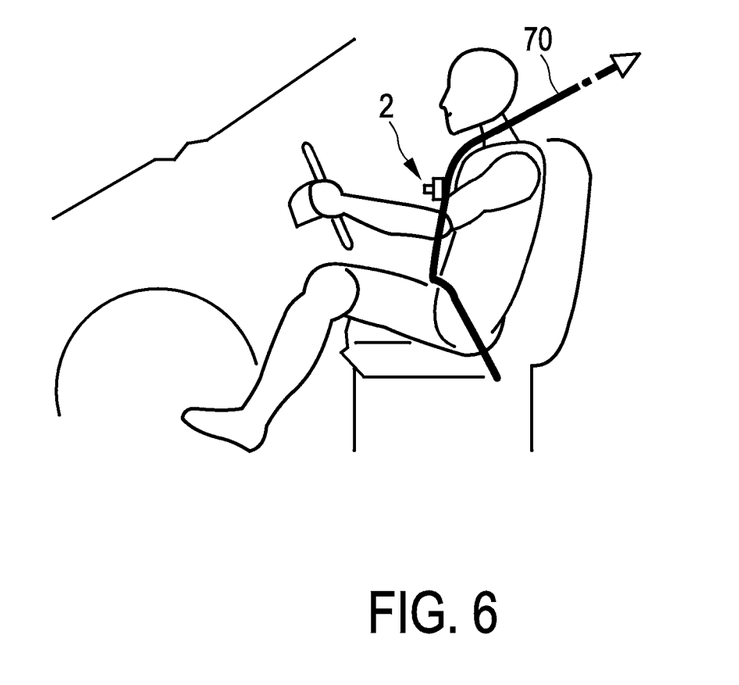
FIG. 6 illustrates a second way of arrangement of the proposed device for a second application.

Another exemplary field of application—drowsiness detection of a driver in a car—is illustrated in FIG. 6. In this scenario the proposed respiration monitoring system, e.g. in the form of a device 2 as illustrated above (or at least the holder and the imaging unit), is, for instance, embedded in or fixed to a seatbelt 70 of a driver (of a car, truck, tram, train; or of a pilot). The imaging unit is able to not only measure a respiratory signal of a driver in a way described above, but also analyze the motion of the driver's hands, visible in the images taken by the imaging unit. The combined analysis of hands motion and respiration allows detection of drowsiness of a driver (e.g. non-moving hands and relaxed respiration), or even further, if the driver is alive and fully awake.

Still another application of the invention lies in the field of sensing extremely shallow movements (e.g. early earthquake detection). By use of the invention motion/movement can be translated into an angular displacement of the imaging unit. Looking/focusing on far away (static) objects or features will cause an amplification of the angular movement and therefore makes it possible to detect even the slightest movement of the imaging unit and/or an object the imaging unit is fixed to. Hence, the invention provides an ultrasensitive motion/movement detector.

In similar other applications the device (e.g. in the form of a smart phone) can be attached to or brought in contact with other objects (or subjects) to measure movement of the object/subject. For instance, the smart phone can be attached to a person or a moving object with the camera looking away from the object to detect movement of the person or the object.

Briefly summarized, the present invention is based on the general idea of measurement of movement/acceleration and/or orientation of a camera based device using a proposed video processing technique and by pointing the camera away from the object that is being measured, i.e. the present invention provides a kind of camera-based accelerometer in a preferred embodiment.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. Device for monitoring movement and orientation of a person, the device comprising:
    an imaging unit for obtaining images over time;
    a holding means for holding said imaging unit to obtain images from the surroundings of the person, wherein the holding means comprises a holder for placing the imaging unit onto the person such that the imaging unit is facing away from the person, and
    a processing unit for detecting movement and orientation of the person based on detecting changes in subsequently obtained images, wherein the detected changes in subsequently obtained images comprise periodic displacements of one or more features of surroundings in the subsequently obtained images for detecting movement of the person.

2. Device as claimed in claim 1, wherein said imaging unit is configured to continuously or at regular intervals obtain images that include still images or video data by use of one or more of a still image camera, video camera and infrared camera.

3. Device as claimed in claim 1, further comprising a connection for allowing the images to be accessed remotely.

4. Device for monitoring movement and orientation of a person, the device comprising:
    an imaging unit for obtaining images over time;
    a holding means for holding said imaging unit to obtain images from the surroundings of the person, wherein the holding means comprises a holder for placing the imaging unit onto the person such that the imaging unit is facing away from the person; and
    a processing unit for detecting movement and orientation of the person by detecting changes in subsequently obtained images, wherein said processing unit is configured to detect periodic displacements of one or more features of surroundings that comprise static marks or gradients of light in the subsequently obtained images for detecting movement that comprises one or more of acceleration and periodic movement of the person.

5. Device for monitoring movement and orientation of a person, the device comprising:
    an imaging unit for obtaining images over time;
    a holding means for holding said imaging unit to obtain images from the surroundings of the person, wherein the holding means comprises a holder for placing the imaging unit onto the person such that the imaging unit is facing away from the person; and
    a processing unit for detecting movement and orientation of the person by detecting changes in subsequently obtained images,
    wherein said holder is arranged for placing the imaging unit onto a person's chest, including onto a clothing or a cover covering the person's chest, such that the imaging unit is facing away from the person's chest to obtain images from the surroundings of the person, and
    wherein said processing unit is configured to detect periodic movements of the person's chest caused by respiration by detecting changes in subsequently obtained images and to determine one or more of the person's respiration rate and respiration volume from the detected movements of the person's chest.

6. Device as claimed in claim 5, wherein said processing unit is configured to determine the person's respiration rate from the period of detected changes in the subsequently obtained images.

7. Device as claimed in claim 5, wherein said processing unit is configured to determine the person's respiration volume from a strength of changes that include an intensity of displacements of one or more features of the surroundings in the subsequently obtained images.

8. Device as claimed in claim 5, wherein a side of the holder facing the person is curved in the form of a hemisphere.

9. Device as claimed in claim 5, further comprising an acceleration measurement unit for determining an acceleration of movements of the person, wherein said processing unit is configured to distinguish periodic movement of the person caused by respiration from other movements of the body based on the subsequently obtained images and to determine the respiration of the person from the determined acceleration of said periodic movements of the subject caused by respiration.

10. Device as claimed in claim 5,
    wherein said imaging unit comprises at least two imaging elements arranged on said holder for individually obtaining images of the person's surroundings, and
    wherein said processing unit is configured to determine the respiration volume of the person by analyzing differences of changes in said individually obtained images.

11. Device as claimed in claim 5,
    wherein said holder is fixed to a seatbelt of a vehicle, and
    wherein said processing unit is configured to detect motion of the hands of the person that is secured by said seatbelt from the subsequently obtained images and to detect drowsiness of the person from a detected motion of the person's hands and one or more of the determined respiration rate and respiration volume of the person.

12. Method for monitoring movement and orientation of a person, the method comprising:
- obtaining images, via an imaging unit, over time, the imaging unit being held, via a holder, onto the person such that the imaging unit is facing away from the person to obtain images from surroundings of the person; and
- detecting, via a processing unit, movement and orientation of the person based on detecting changes in subsequently obtained images, wherein the detected changes in subsequently obtained images comprise periodic displacements of one or more features of surroundings in the subsequently obtained images for detecting movement of the person.

13. A non-transitory computer-readable medium embodied with a computer program that comprises program code for causing a computer to carry out the steps of the method as claimed in claim 12, in response to said computer program being carried out on the computer.

14. Processor for use in a device for monitoring movement and orientation of a person, the device comprising an imaging unit facing away from the person for obtaining images over time from surroundings of the person, said processor being configured to detect movement and orientation of the person based on detecting changes in subsequently obtained images, wherein the detected changes in subsequently obtained images comprise periodic displacements of one or more features of surroundings in the subsequently obtained images for detecting movement of the person.

15. Processing method for use in a device for monitoring movement and orientation of a person, the method comprising:
- holding, via a holder, the device that comprises an imaging unit facing away from the person for obtaining images over time from the surroundings of the person; and
- detecting, via a processor, movement and orientation of the person lay-based on detecting changes in subsequently obtained images, wherein the detected changes in subsequently obtained images comprise periodic displacements of one or more features of surroundings in the subsequently obtained images for detecting movement of the person.

\* \* \* \* \*